United States Patent [19]

Inerte

[11] 4,314,574
[45] Feb. 9, 1982

[54] TOOTH-PICK HAVING ONE FOLDED END AND ASSOCIATED POCKET CONTAINER BOX

[76] Inventor: Maria Inerte, Via S. Bernardino, 152, Bergamo, Italy

[21] Appl. No.: 81,852

[22] Filed: Oct. 4, 1979

[30] Foreign Application Priority Data

Oct. 5, 1978 [IT] Italy .............................. 22957/78[U]

[51] Int. Cl.³ .............................................. A61C 15/00
[52] U.S. Cl. .......................................... 132/89; 132/93
[58] Field of Search ................. 132/89, 93; 206/56 A, 206/56

[56] References Cited

U.S. PATENT DOCUMENTS

| 86,637 | 2/1869 | Bowser | 132/90 |
|---|---|---|---|
| 3,650,392 | 3/1972 | Haagedoorn | 132/89 |
| 4,135,528 | 1/1979 | Stark | 132/89 |

FOREIGN PATENT DOCUMENTS

| 604677 | 1/1974 | Switzerland | 132/89 |
|---|---|---|---|
| 191896 | 1/1923 | United Kingdom | 132/89 |

Primary Examiner—G. E. McNeill
Attorney, Agent, or Firm—Young & Thompson

[57] ABSTRACT

Tooth-picks formed by a straight central portion of constant thickness, an end with a sharp point or tip, another end with a section angled at about 45° with thickness tapering to the tip, which is transversally rounded.

They can be housed in a pocket container of a flat parallelepiped shape closed by a T-shaped cap.

2 Claims, 5 Drawing Figures

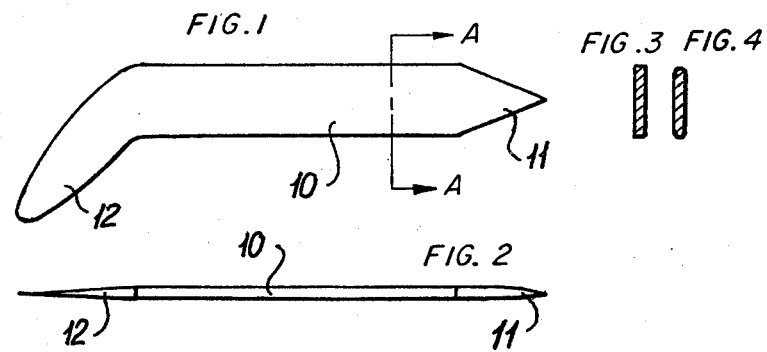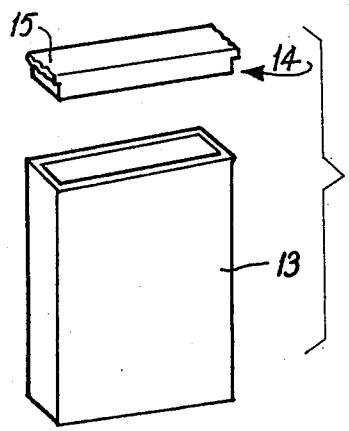

TOOTH-PICK HAVING ONE FOLDED END AND ASSOCIATED POCKET CONTAINER BOX

This invention relates to a tooth-pick having one angled end and an associated pocket container.

Tooth-picks are commonly known, as mostly made of wood or plastics material, having round, square or plain or flat section, but provided with the two ends that are mirror-like the same relative to a plane perpendicular to the single longitudinal axis of symmetry.

Some of such tooth-picks are characterized by being provided with a sharp point or tip, and others by having a rounded point or tip.

A tooth-pick according to the present invention combines the advantages of both of the above mentioned types but with the added novelty of having one end thereof angled, so as to be of asymmetrical shape, with one end of prevailingly pointed configuration and the other end of prevailingly rounded configuration, but with a blade thickness.

The cross-section may be reactangular with sharp edges or chamfered edges; it is of constant thickness towards the sharpened point or tip, while gradually decreasing to the opposite end with a resulting tapering, promoting entry into the intertooth space.

Many are the advantages to be found in using the present invention:

the inclined or angled section allows an easy access to all of the tooth interstices, thus obtaining an improved cleaning of the oral cavity.

The least tapered end is intended for the intertooth spaces, while the pointed or sharpened end of the opposite end, which is of constant thickness, is more useful adjacent the tooth neck or on the occlusal surfaces.

The present invention may be made of different materials, such as for example plastic or metal, which are thoroughly smoothed out to avoid any unevenness which would be a danger for the gums.

The advantages in using the present invention are such that nobody, after experiencing them would tolerate the use of the tooth-picks as hitherto used on a dinner table, as gathered in an open container and hence unhygenic. According to the invention, it was deemed convenient to further provide a personal flat box of minimum overall size, providing the possibility of keeping in a hygienically protected manner some tooth-picks for exclusively personal use, which can accordingly be always carried in one's pocket, hand-bag or the like and taken out at suitable time and not before other persons.

For example, said box may be of flat parallelepidedal shape, open at one of the two minor sides. A cap is pressure inserted therein, with at least one small laterally projecting tab or flange to facilitate the box opening. However, it should be understood that the box could also be made as a small envelope of plastic, leather or skin or any other material.

The present invention will be more clearly understood from the accompanying drawing given by mere way of unrestrictive illustration, and in which:

FIG. 1 is a side, plan and sectional view showing the tooth-pick;

FIG. 2 is a plan view thereof;

FIGS. 3 and 4 are cross sections, taken on the line A—A of FIG. 1, showing two different embodiments; and FIG. 5 is a perspective view showing the container with its raised cap.

In the side elevational view of FIG. 1, there is shown a straight central body 10, on one side terminating in a sharp point or tip 11 whose thickness is constant.

At the opposite end, the axis sharply shifts about 45°. The thickness gradually decreases, as shown in FIG. 2, and the tip or point 12 terminates with a rounded edge.

The two cross-sections of FIGS. 3 and 4 show two of the possible embodiments with sharp or rounded edges.

FIG. 5 shows the bottom 13 with the cap 14 at the top shown in raised position. Said bottom 13 comprises a simple parallelepiped with narrow sides, open at the top. Cap 14 is pressure inserted in this opening, the cap being T-shaped due to the two small side tabs 15, slightly projecting from the box when the cap is in place, in order to facilitate a ready opening of the box, even with only one hand.

The box may also be made of the most various materials from plastic to precious metals and may be made rigid or flexible.

I claim:

1. The combination of a laminar toothpick with a pocket container, both said toothpick and said container being flat and lying substantially in the same plane, the container walls and the laminar toothpick contacting each other inside said container, the toothpick comprising a straight central portion of a constant thickness, terminating at one end in a sharp point, while the other end is angular, lying in the same plane but disposed at about 45° to the axis of said central portion, said point and said angular end being integral with said central portion, said angular end having adjacent the first portion the same thickness as the central portion, but thence immediately tapering, toward the tip, and terminating in a rounded edge.

2. A laminar toothpick comprising a straight central portion of a constant thickness, terminating at one end in a sharp point, while the other end is angular, lying in the same plane but disposed at about 45° to the axis of said central portion, said point and said angular end being integral with said central portion, said angular end having adjacent the first portion the same thickness as the central portion, but then immediately tapering, toward the tip, and terminating in a rounded edge.

* * * * *